United States Patent [19]

McRae

[11] Plant 4,178

[45] Jan. 3, 1978

[54] LILY PLANT: LILIUM 'LOVESONG'

[75] Inventor: Edward A. McRae, Boring, Oreg.

[73] Assignee: Melridge, Inc., Gresham, Oreg.

[21] Appl. No.: 761,229

[22] Filed: Jan. 21, 1977

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Eugene D. Farley

[57] ABSTRACT

A new variety of Asiatic hybrid lily plant unique in its division and having unusually bushy, lush foliage borne on a single erect stem and having a large number of buds and flowers, both characterized by a brilliant scarlet color.

1 Drawing Figure

BACKGROUND OF THE INVENTION

My new variety of lily plant originated as a seedling selected from a group of seedlings at Gresham, Oreg. The seedlings were planted as part of a breeding program carried on by me since the year 1966. This program had as its primary objectives the production of superior upright red lilies, with improved flower color and a more outstanding plant habit, in particular vigorously growing, strong, upright Asiatic red lilies having bushy foliage and being genetically short enough for pot culture without chemical treatment.

I achieved the desired objective by using as a seed parent Lilium 'Byam's Ruby' and as the pollen parent Lilium 'Red Carpet'.

The new lily plant resulting from my breeding efforts is single stemmed, erect and very bushy. It grows to a height of only 18 to 20 inches from a bulb 5 to 7 inches in circumference, and hence it is ideal for pot culture. Its strength is outstanding.

The foliage of my new lily plant is abundant and comprises a multiplicity of lanceolate leaves 4 to 5 inches long which are a glossy deep green color. The unusual length and number of leaves gives my new plant a "Christmas tree" effect. The number of buds borne by my new plant is very high, being 8 to 12 buds per stem produced from a bulb 5 to 7 inches in circumference. Both flowers and buds, when the tepals first divide and unfurl, are a most striking clearest deep scarlet in color.

My new plant is also exceptional in the vigor of its growth, its rapid propagation, its resistance to disease, and its tolerance of infection by virus, and its longevity. It is outstanding in its suitability for pot culture, all as observed by me at Gresham, Oreg.

My new variety of lily plant has been asexually reproduced by me and under my direction at Gresham, Oreg. Successive generations produced by bulb scale propagation and natural propagation from bulblets and division have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the upper portion of the plant including the stem, foliage, and flower cluster with the buds in various stages of opening and certain of the flowers in full bloom. The drawing shows in particular the vivid deep scarlet color of the flower.

DESCRIPTION OF THE NEW VARIETY

The following is a detailed description of my new variety of Asiatic hybrid lily, with nomenclature according to *The International Lily Register* (Royal Horticultural Society, London, 1969) and with color designations according to the Royal Horticultural Society Color Chart, published by the Royal Horticultural Society in 1966.

THE PLANT

Origin: Seedling.
Parentage:
- *Seed parent.*—Lilium X 'Byam's Ruby' (unpatented).
- *Pollen parent.*—Lilium X 'Red Carpet' (unpatented).

Classification:
- *Botanic.*—Hybrid Lilium cultivar; Division 1-A of Horticultural Classification of Lilies of the R.H.S.
- *Commercial.*—Asiatic hybrid lily.

Form: Single stem, erect and very bushy.
Height: 18 to 20 inches from bulbs 5 to 7 inches in circumference.
Growth: Very vigorous and upright.
Strength: Excellent.
Foliage:
- *Quantity.*—Abundant.
- *Size of leaf.*—4 to 5 inches long.
- *Shape of leaf.*—Lanceolate.
- *Texture.*—Leathery and glossy.
- *Color.*—Upper and undersides both deep green.

Bulbs:
- *Size.*—Any size ranging up to 12 inches in circumference.
- *Color.*—White.

THE BUD

Form: Obtuse; long and urn-shaped.
Size: 2 to 2½ inches long and about 1½ inches in circumference at maturity.
Opening: Bud opens slowly.
Color: Clearest deep scarlet when the tepals first divide and when they begin to unfurl.
Tepals: Curl back; clearest deep scarlet both on the inside and on the outside.

Peduncle: 1 to 2 inches long; hairy; erect; in color, dark green with reddish tinge.

THE FLOWER

Blooming habit: Blooming habit recurrent; annually in mid-season; blooms once and profusely.
Size: Medium; about 5 inches in diameter.
Borne: In clusters, from 6 to 12 on a single stem from a bulb 5 to 7 inches in circumference.
Shape: Flat, with petals reflexing only slightly.
Tepalage:
*Number of tepals.*—6.
*Arrangement.*—Imbricated.
*Color.*—Outer tepal clearest scarlet, inside tepal deepest scarlet, reverse side of tepal deepest scarlet, base deeper scarlet, all in the range of R.H.S. C.C.34A-B. Narrow gold silver evident above each nectary.
*Tepal longevity.*—Tepals stay on stem about 3 weeks.
Spotting: Lightly spotted with a few tiny black spots at the bases of the tepals only.
Pedicel:
*Length.*—1 to 2 inches.
*Color.*—Deepest green with reddish brown coloring.
*Form.*—Pedicel is sturdy and upright.
Color change: Flower color fades slightly to mahogany red with age.
Appearance: The flower is shiny.
Disease resistance: The flower and plant are exceptionally resistant to disease, particularly to Fusarium and Botrytis.
Fragrance: The flower is not fragrant.
Lasting quality: The flower is long lasting both on the plant and as a cut flower.

THE REPRODUCTIVE ORGANS

Stamens, anthers:
*Arrangement.*—Typical of Liliaceae.
*Length.*—About 2 inches.
*Number.*—6.
*Filaments.*—2 inches long; color reddish.
Pollen and Anthers: Cinnamon in color.
Pistils: One in number with a length of about 2 inches.
Stigma: Reddish brown in color.
Characteristics of ovaries: Typical of genus Lilium.

THE FRUIT

Fertility: The fruit is fertile.
Shape: The fruit is ovoid.
Color at maturity: The fruit is soft brown.

My new variety of Asiatic hybrid lily most nearly resembles the variety Lilium cultivar 'Cinnabar' (unpatented), but is distinguished from it in its unusual bushiness with lush foliage, its high degree of disease resistance and virus tolerance, its longevity, its shorter stature and suitability for pot culture, its greater number of flowers, and in particular by the intense deep scarlet of its flowers.

I claim:

1. A new and distinctive variety of Asiatic hybrid lily plant substantially as herein shown and described, characterized by its short to medium height, its bushiness, its abundant foliage comprising lanceolate deep green leaves, the vigor of its growth, the rapidity of its propagation, its resistance to disease and tolerance to virus, its longevity, its suitability for pot culture, and in particular the vibrant clear deep scarlet color of its buds upon dividing and unfurling and of its flowers when the plant is in full bloom.

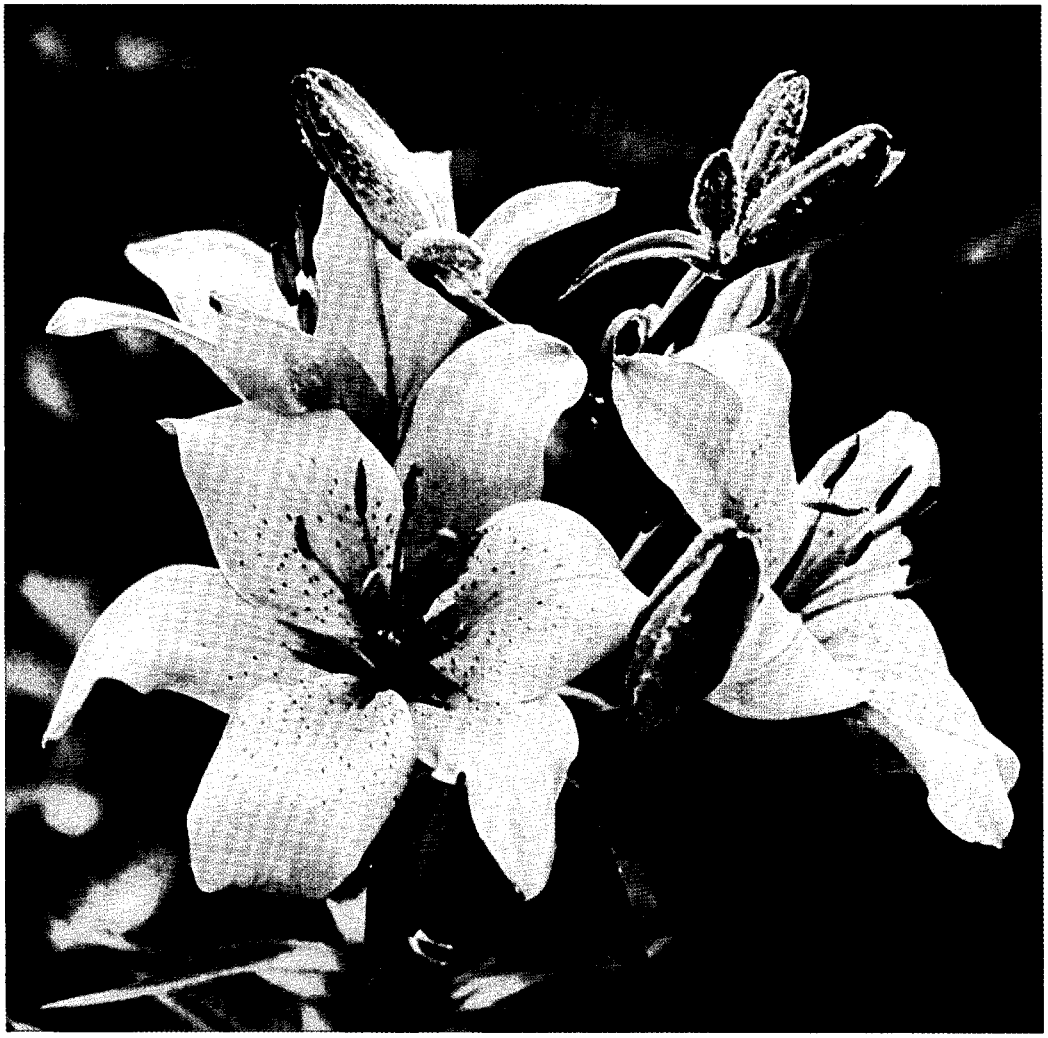

* * * * *